United States Patent [19]
le Roux Murray

[11] Patent Number: 4,888,956
[45] Date of Patent: Dec. 26, 1989

[54] CRYOGENIC APPARATUS AND CRYOGENIC METHODS

[76] Inventor: Pieter W. le Roux Murray, Private Bag X41, Pretoria, 0001, South Africa

[21] Appl. No.: 144,121

[22] Filed: Jan. 15, 1988

[30] Foreign Application Priority Data

Jan. 16, 1987 [ZA] South Africa .................. 87/0318
Sep. 4, 1987 [ZA] South Africa .................. 87/6629

[51] Int. Cl.⁴ .................................... F25B 19/00
[52] U.S. Cl. ................................ 62/51.1; 62/63; 62/64
[58] Field of Search ............... 62/78, 514 R, 63, 64, 62/57, 51.1; 34/5

[56] References Cited

U.S. PATENT DOCUMENTS

| | | | |
|---|---|---|---|
| 3,228,838 | 1/1966 | Rinfret et al. | 62/78 |
| 3,681,851 | 8/1972 | Fleming | 34/5 |
| 3,738,121 | 6/1973 | Swindell | 62/57 |
| 4,302,950 | 12/1981 | Sitte | 62/78 |
| 4,470,202 | 9/1984 | Buxton et al. | 34/5 |
| 4,485,641 | 12/1984 | Angelier et al. | 62/78 |
| 4,537,034 | 8/1985 | Crouch | 62/78 |
| 4,704,873 | 11/1987 | Imaike et al. | 62/78 |
| 4,723,420 | 2/1988 | Sitte | 62/514 R |

FOREIGN PATENT DOCUMENTS

2117222 10/1983 United Kingdom .

OTHER PUBLICATIONS

R. I. Taylor, "A New Cryogenic Process for the Food Industry", Before 1984, pp. 231-240.
Murray, "Accurate Control of Cryogen Temperature for Quick Freezing of Biological Tissue", 10/12/86, four pages.
KF 80 Universal Cryofixation System, 10/12/86, four pages.
Maja-Maschinenfabric, Hermann Schill GmbH, MAJA Scherbeneis, six pages.
Sandvik France, Department Transporteurs, SANDVIK, four pages.

Primary Examiner—Ronald C. Capossela
Attorney, Agent, or Firm—Bernard, Rothwell & Brown

[57] ABSTRACT

Cryogenic apparatus and methods are disclosed which enable a substance to be frozen at a rapid rate thereby promoting the formation of a multitude of small ice crystals in the substance rather than a smaller number of large ice crystals. The method comprises circulating a cryogen around a closed canal. The canal is preferably partly immersed in a bath containing a liquid which boils at a temperature below the boiling point of the cryogen in the canal, and which preferably boils at a temperature below the freezing point of the cryogen in the canal. Means for sensing the temperature of the cryogen are provided, the temperature sensing means controlling a heater which maintains the temperature of the cryogen above its freezing point. The cryogen can circulate in a horizontal plane or in a vertical plane. Where the substance to be frozen comprises organic tissue, the cryogen preferably flows in a vertically arranged canal and the tissue is plunged countercurrent into upwardly flowing cryogen. Where the substance to be frozen is a material consisting of two or more homogeneously mixed components, then the material is preferably introduced into the cryogen as a series of drops or as a fine continuous stream which falls on the flowing surface of the cryogen. The method is particularly suitable for the preparation of ceramics, potassium superoxide and catalysts.

19 Claims, 3 Drawing Sheets

CRYOGENIC APPARATUS AND CRYOGENIC METHODS

This invention relates to cryogenic apparatus and cryogenic methods.

BACKGROUND TO THE INVENTION

Low temperature techniques have found extensive uses in industry, in laboratories, and in the medical field.

The freezing of tissue samples prior to the preparation of biological samples for electronmicroscopy is an example of the use of a low temperature technique. The sample is normally plunged into boiling liquid nitrogen or into a cryogen such as one of the Freons that has been cooled down to a temperature below its boiling point.

It is well known that repeatability is an important feature in the freezing of biological tissue. If one sample is to be comparable with another then the factors which influenced the way in which the tissue froze must be as identical as possible in each case. Ice crystal formation in the tissue sample as it is being frozen is a cause of non-repeatability. A rapid rate of cooling is essential because slow cooling has the effect of promoting the growth of large ice crystals which lower the usefulness of the tissue sample due to deformation of its cell structure and redistribution of chemical components in the tissue. Fast cooling rates produce more ice crystals of smaller size with reduced tissue deformation.

The present invention seeks to provide cryogenic apparatus and a cryogenic method which enable experimental repeatability to be achieved where this is desired, and which also enable rapid freezing, and hence the elimination of large ice crystals, to be obtained.

Another use of cryogenic techniques involves introducing into, for example, boiling liquid nitrogen a material which has two or more components that have been homogeneously dispersed in the material by, for example, mechanical mixing. The components are dispersed in a liquid carrier medium, usually water, and the purpose of dripping them into boiling liquid nitrogen is to freeze the water as rapidly as possible. The frozen material is then subjected to sublimation i.e. is freeze dried to remove the water. The purpose of adopting this technique is to reduce re-distribution of the components of the material with respect to one another as a result of the growth of large ice crystals, which has the effect of destroying the homogenity which has been achieved by mixing. The more rapid the cooling the smaller and more numerous the ice crystals that are formed. Slow cooling results in the formation of a smaller number of large ice crystals, the larger ice crystals displacing the components of the mixture and resulting in the mixture being non-homogeneous. The purpose of the freeze drying step is to avoid the carrier medium returning to its liquid state during the drying process as this would result again in a rearrangement of the components.

Such techniques find application in the production inter alia of ceramics such as Beta Alumina ceramic, potassium superoxide, and catalysts.

BRIEF DESCRIPTION OF THE INVENTION

According to one aspect of the present invention there is provided cryogenic apparatus comprising walling bounding an endless canal for containing liquid cryogen, means for continuously circulating liquid cryogen around said canal so that it flows past an entry location, and means for introducing a substance to be frozen into the canal at said entry location so that it contacts the cryogen flowing past the entry location and is frozen by it.

In one form the apparatus includes a bath in which said canal is located, the bath serving to hold a liquid which boils at a temperature below the freezing point of the cryogen in the canal, means for detecting the temperature of the cryogen, and heating means for maintaining the temperature of the cryogen above its freezing point but sufficiently far below its boiling point to prevent boiling occurring when the substance to be frozen is introduced.

In another form said canal is bounded by an upwardly open container for receiving liquid cryogen and by a vertical partition in said container, said means for continuously circulating liquid cryogen being arranged to displace it upwardly on one side of the partition so that it flows over the upper edge of the partition, then downwardly on the other side of the partition and thence back to said one side of the partition.

In yet another form said apparatus further comprises means above said entry location for supplying, in the form of drops or as a continuous stream, the substance to be frozen whereby the substance falls onto the surface of the flowing cryogen, and means spaced from said entry location for recovering from the cryogen the substance after it has been frozen. In this constructional form the apparatus can further include a receptacle for receiving the recovered frozen substance, the receptacle being such that it can be evacuated to a pressure low enough to cause sublimation of any water in said recovered frozen substance.

In a preferred form of said cryogenic apparatus said canal is bounded by a container having side and end walls and a bottom wall, a spacer in said container, the spacer being spaced from said end and bottom walls of the container whereby the canal passes upwardly between the spacer and an end wall, over the top of the spacer, downwardly between the spacer and the other end wall, and then between the spacer and the bottom wall.

Desirably, at least part of the upper surface of said spacer slopes whereby cryogen flows down said sloping surface, said entry location being above the spacer.

In another embodiment, said canal is bounded by inner and outer endless vertical walls the lower ends of which are joined by a bottom wall, said continuously circulating means being an impeller positioned between said inner and outer vertical walls.

According to another aspect of the present invention there is provided a method of treating a material consisting of at least two components which comprises preparing a homogeneous dispersion of the components in a liquid carrier, feeding the material onto the surface of flowing liquid cryogen at an entry location, recovering the frozen material from the cryogen at a location spaced from the entry location, and sublimating the frozen material.

According to a further aspect of the present invention there is provided a method of freezing a tissue sample which method comprises circulating liquid cryogen upwardly on one side of a vertical partition so that it flows over the partition, down the other side of the partition and thence back to said one side of the partition, and plunging said tissue sample downwardly into the cryogen which is flowing upwardly on said one side of the partition.

Preferably, according to this method, said liquid cryogen flows upwardly inside a cylindrical member and then radially outwardly in all directions to flow over the upper edge of the cylindrical member, and said tissue sample is plunged downwardly along a line which is co-incident with the axis of said cylindrical member.

BRIEF DESCRIPTION OF THE DRAWINGS

For a better understanding of the present invention, and to show how the same may be carried into effect, reference will now be made, by way of example, to the accompanying drawings in which.

DETAILED DESCRIPTION OF THE DRAWINGS

Figure 1:
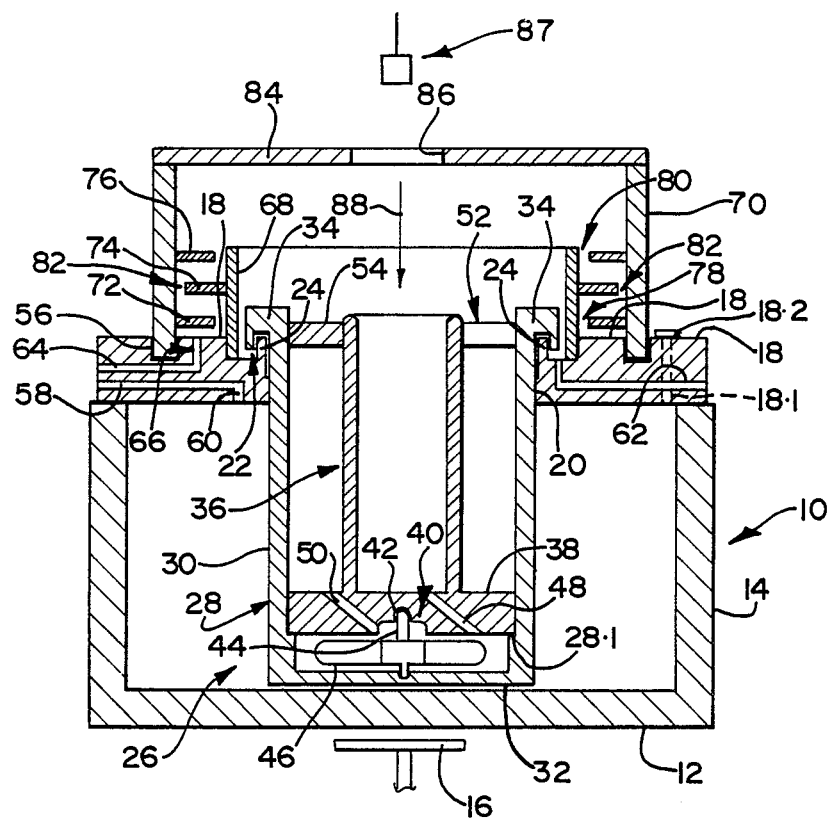
FIG. 1 is a vertical section through cryofixation apparatus.

The cryofixation apparatus illustrated in FIG. 1 comprises a bath 10 for receiving boiling liquid nitrogen, the bath 10 comprising a circular base 12 and a cylindrical side wall 14. The bath 10 is upwardly open. A magnetic stirrer 16 is provided below the base 12. The upper end of the bath 10 is closed by a horizontal plate 18 which has a circular central opening 20 therein. A circular groove 22 is co-axial with the opening 20, the provision of the groove resulting in the formation of a peripheral flange 24 which encircles the opening 20. The remaining features of the plate 18 will be described in more detail hereinafter.

A cryogen container generally designated 26 comprises an upwardly open outer cylinder 28 having a cylindrical side wall 30 and a circular base 32. The open upper end of the side wall 30 is encircled by a rim 34. The rim 34 seats on the flange 24 so that the cylinder 28 hangs from the flange 24 with its base 32 above the base 12 of the bath 10. The depending part of the rim 34 is in the groove 22. This inhibits flow of evaporated or spilt cryogen into the bath 10.

Within the cylinder 28 there is a tubular member 36 constituting a vertical partition. At the lower end of the member 36 there is a radially outwardly directed flange 38 which is a sliding fit within the cylinder 28. Downward sliding movement of the member 36 is limited by an internal seat 28.1 of the cylinder 28. The underside of the flange 38 is provided with a dome-shaped downwardly open central recess 40. The recess 40 is extended upwardly by a blind bore 42 which forms a mounting for the top end of a shaft 44 of an impeller designated 46. The lower end of the shaft 44 is seated in a blind bore in the base 32. The impeller 46 is preferably a Teflon coated magnet.

Two circular arrays of bores are provided in the flange 38. In the drawing only one bore of each array is shown, these bores being designated 48 and 50. Each bore 48 slopes upwardly from the lower, outer periphery of the flange 38 and opens into the cylindrical space bounded by the tubular member 36. Each bore 50 leads from the top face of the flange 38 at a position radially outwardly of the tubular member 36 and opens into the recess 40.

If desired the shaft 44 can be omitted and the impeller 46 can simply lie loosely in the space below the member 36. In this form the recess 40 and the blind bores for the shaft 44 are omitted, and the bores 50 open in a circular array through the central part of the flat underface of the flange 38.

The tubular member 36 further includes an upper flange 52 which is a sliding fit in the cylinder 28. The flange 52 consists of a number of radially extending fins 54 with gaps between them. Previously plunged specimens can be stored by "hanging" them from the fins 54 so that they are within the annular space between the cylinder 28 and the tubular member 36.

Reverting now to the plate 18, this, in addition to the groove 22 and flange 24, comprises a second groove designated 56. A passage 58 is drilled horizontally in the thickness of the plate 18 and a port 60 connects the passage 58 to the interior of the bath 10. A second passage 62 in the thickness of the plate 18 leads into the groove 22 and a third passage 64 in the thickness of the plate communicates, via a port 66, with the space above the plate 18. A filler passage 18.1 closed by a plug 18.2 is provided for enabling the bath 10 to be filled with liquid nitrogen and to be topped-up as necessary. If desired the passage 64 can be close to the passage 18.1 so that the passage 18.1 and the plug 18.2 are heated and frosting up prevented.

Inner and outer cylinders 68 and 70 stand in the grooves 22 and 56. The cylinder 70 is taller than the cylinder 68.

Three baffle rings 72, 74 and 76 are located in the annular space between the cylinders 68 and 70. As will clearly be seen from the drawing, the lower ring 72 is a tight fit in the outer cylinder 70 but there is an annular gap 78 between it and the cylinder 68. The upper ring 76 is similarly located and the gap between it and the inner cylinder 68 is designated 80. The intermediate ring 74 is a tight fit on the cylinder 68 and there is an annular gap 82 between it and the cylinder 70. More or less than three rings can be provided if desired. The baffle rings 72, 74 and 76 can also be replaced by one or more rings of porous material located between the cylinders 68 and 70.

A lid 84 having a central opening 86 rests on the outer cylinder 70. The upper end of the cylinder 68 is thus below the lower surface of the lid 84.

The passage 58 communicates with the passage 64 by way of a heat exchanger or heater (not shown in FIG. 1). If a heat exchanger is used, this can consist of a simple coil in a bath of water which is maintained at ambient temperature.

A heater element (not shown) is provided in the annular space between the member 36 and the cylinder 28. The heating element is controlled by an electronic circuit which includes a sensor which monitors the temperature of the cryogen. By applying energy in the form of heat to the cryogen its temperature can be maintained constant, preferably close to its freezing point.

Magnetic coupling between the stirrer 16 and impeller 46 is preferred but any other suitable system for rotating the impeller 46 can be used.

In use of the cryofixation apparatus, the magnetic stirrer 16 is rotated and this in turn rotates the impeller 46. The impeller continuously draws cryogen from the recess 40, feeds it outwardly, and pumps it upwardly through the bores 48 into the centre column constituted by the tubular member 36 from whence it flows over the upper edge of the member 36. Cryogen forced outwardly from the recess 40 is replaced by cryogen drawn from the cylindrical space between the cylinder 28 and the member 36 through the bores 50. Circulation of the cryogen around the canal comprising the tubular member 36, the space between the cylinder 28 and the member 36 and the bores 48 and 50 ensures that it is continuously thoroughly stirred and is thus of substantially uniform temperature throughout.

The bath 10 is filled with boiling liquid nitrogen, this cooling the cryogen (which can be inter alia propane or one of the Freons). Stirring and heating of the cryogen ensures that while its temperature is lowered to very close to its freezing point, the cryogen does not freeze. The cryogen flows upwardly in the tubular member 36 and then radially outwardly, in a completely symmetrical pattern, over the circular wier constituted by the upper edge of the tubular member 36. Flow is laminar without any rotational component. The cryogen which flows over the wier enters the space between the member 36 and the cylinder 28 via the gaps between the fins 54.

Cold nitrogen gas which boils off the liquid in the holder 10 escapes through the port 60 and passage 58. It passes through the heater or the heat exchanger and its temperature is raised to ambient or at least to above 0 degrees C. A part or all of this gas then returns, via the passage 64, to the annular space between the cylinders 68 and 70, The baffles constituted by the rings 72, 74 and 76 ensure that, at the gap 80, the nitrogen pressure is substantially constant around the entire periphery of the inner cylinder 68 and is close to atmospheric. There is thus a symmetrical flow of ambient temperature nitrogen gas radially inwardly towards the axis of the system. Some of the gas flows upwardly through the opening 86 and the remaining gas flows downwardly towards the surface of the cryogen. As it approaches the cryogen surface it turns radially outwardly and flows, with cryogen gas that has evaporated, into the groove 22. From the groove 22 it flows through the passage 62 to atmosphere.

The mechanical construction which holds the sample and plunges it into the tubular member 36 through the opening 86 has been illustrated at 87 and can be of any conventional type. The line along which the sample is plunged to the entry location is shown at 88, this line co-inciding with the axis of the member 36.

Figure 2:
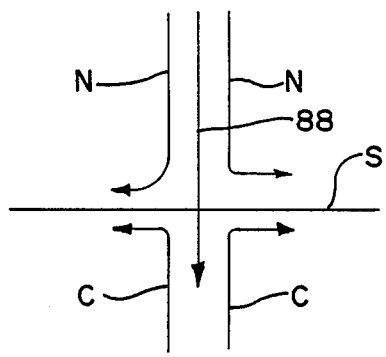
FIG. 2 illustrates the flow pattern at the cryogen surface.

Experimental work has shown that the central space above the liquid cryogen is substantially filled with dry nitrogen at above 0 degrees C. The only cold surface in the space above the cryogen is the rim 34 of the bath 36. The absence of water vapour in the vicinity of this rim prevents it frosting. Only immediately above the liquid cryogen is there any possibility of there being a layer of cold cryogen gas. Any layer which does exist is extremely thin due to the fact that both the cryogen and the dry nitrogen gas flow radially outwards at the interface between the cryogen and the gas from the point at which the axis of the tubular member 36 intersects the cryogen surface. This is also the point at which the sample being plunged enters the cryogen. In FIG. 2 the cryogen surface is designated S. Arrows N designate the flow of nitrogen gas and arrows C the flow of liquid cryogen. Cryogen in a gaseous state above the surface of the liquid cryogen is swept away radially from the intersection point by the nitrogen gas and by the flowing liquid cryogen which exerts a dragging action on evaporated cryogen molecules which are above the liquid surface. The line 88 along which plunging occurs is also shown in FIG. 2. Attention is drawn to the fact that flow of cryogen along this line is vertical and without any rotational component.

The cryogen flowing upwardly in the tubular member 36 follows a symmetrical pattern. There is linear flow up to the surface of the cryogen and then symmetrical flow radially outwardly over the weir. The construction described ensures that there is insignificant pre-cooling of the sample due to cold gas above the liquid cryogen, and that the sample being plunged always enters cryogen which is flowing in a predetermined continuously constant and repeatable pattern. More specifically the cryogen has a fixed uniform temperature, it flows vertically and the sample enters it vertically so that accurate countercurrent plunging is obtained, and there is insignificant precooling in view of the fact that there is little evaporated cryogen gas above the liquid cryogen. The experimental variables which result in the freezing pattern of samples varying from sample to sample are thus substantially eliminated.

The previously plunged specimens hanging from the fins 54 are maintained frozen but do not interfere with cryogen circulation.

Figure 3:
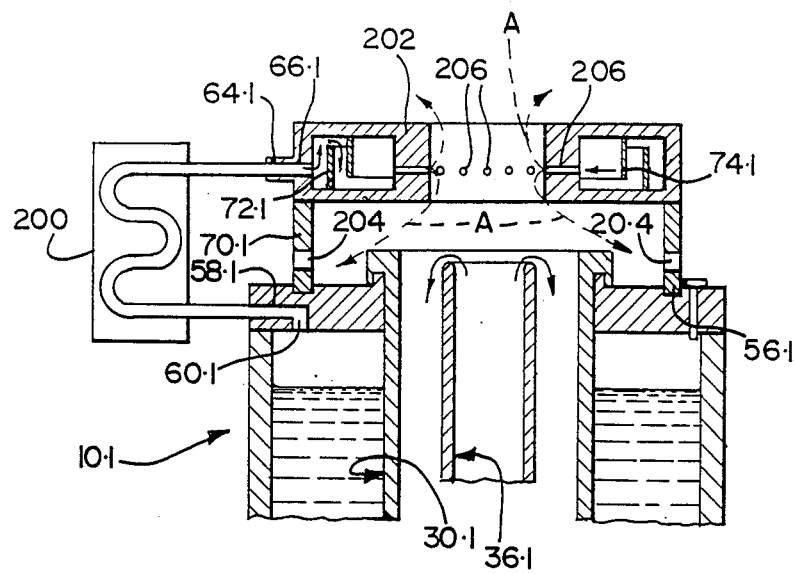
FIG. 3 illustrates the upper part of a modification of the apparatus of FIGS. 1 and 2.

Referring now to FIG. 3, parts which are equivalent to those illustrated in FIG. 1 have been designated with the same reference numeral plus the suffix 0.1.

The passage 58.1 which leads from the port 60.1 is connected to a heat exchanger 200 which raises the temperature of the cold nitrogen gas to ambient. The gas emerging from the heat exchanger 200 enters the passage 64.1 and emerges through the port 66.1 into the structure which has been designated 202. The structure 202 is mounted on a cylinder 70.1 the lower edge of which seats in the groove 56.1.

The cylinder 70.1 has a ring of holes 204 through which gaseous nitrogen and evaporated cryogen can escape.

Within the structure 202 there are vertical rings 72.1 and 74.1 which define a tortuous path between the port 66.1 and a ring of radial passages 206 formed in the structure 202.

The arrows A in FIG. 3 designate the way in which ambient temperature nitrogen emerging through the passages 206 flows. It will be seen that it flows both upwardly out of the structure 202 and downwardly into the space bounded by the cylinder 70.1 prior to escaping through the holes 204.

The nitrogen sweeps away evaporated cryogen and ensures that the sample being plunged remains at a temperature above the freezing point of water until it enters the cryogen which is flowing upwardly in the tubular member 36.1.

Figure 4:
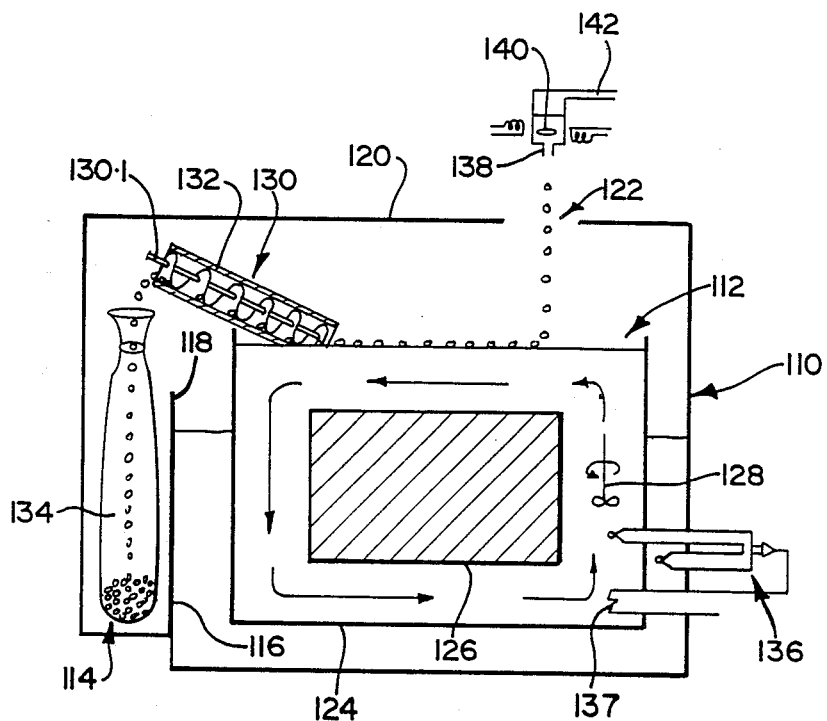
FIG. 4 is diagrammatic side elevation of apparatus for treating a ceramic material.
Figure 5:
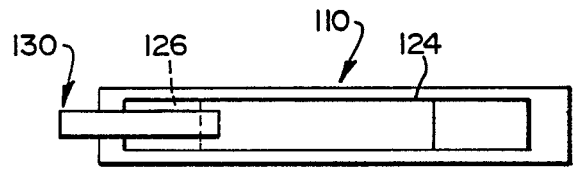
FIG. 5 is a top plan view of part of the apparatus of FIG. 4.

The apparatus of FIGS. 4 and 5 comprises a bath 110 defining a main compartment 112 and a subsidiary compartment 114. A wall 116 between the two compartments has a top edge 118 which is above the level of the boiling liquid nitrogen in the bath 110. The bath 110 further comprises a top plate 120 which has an opening 122 in it. The shape of the bath 110, when viewed in plan, can be seen from FIG. 5.

Within the bath 110 there is a container 124, the walling of the container 124 being spaced from the walling of the bath 110. The means for locating the container in position have not been illustrated. Within the container there is a spacer 126. Between the spacer 126 and the walling of the container 124 there is an impeller 128 which causes liquid cryogen in the container 124 to circulate. More specifically, as shown by the arrows, the impeller 128 causes liquid cryogen to flow upwardly on one side of the spacer 126, across the top of the spacer, down the other side of the spacer, and then beneath the spacer. The shape of the canal around which the cryogen circulates is such that there are no dead spots where cryogen is at rest and where freezing can start. The impeller 128 induces turbulence which results in thorough mixing.

An Archimedean screw 130 is located in the bath 110 with its lower end in the container 124. The position of the screw 130 is such that its lower end is, in use, immersed in liquid cryogen in the container 124. In a preferred constructional form the screw 130 comprises the screw proper designated 130.1 and a cylindrical casing which has been designated 132, the screw 130.1 preferably being a relatively loose fit in the casing 132.

Within the subsidiary compartment 114 there is a vessel diagrammatical illustrated at 134. The vessel 134 is sufficiently strong to enable it to be evacuated after removal from the apparatus.

Reference numeral 136 diagrammatically indicates temperature sensing means which are provided for determining the difference between the temperature of the cryogen in the container 124 and temperature of the boiling liquid nitrogen in the bath 110. A heater 137 in the container 124 is controlled by the sensing means 136 and ensures that the temperature of the cryogen remains just above its freezing point.

Above the opening 122 there is a nozzle diagrammatically shown at 138 with a stirrer 140 (preferably a magnetic stirrer) upstream of the nozzle 138. A pipe 142 leads to a pump (not shown) which supplies material to the nozzle under pressure. Any other means for feeding material in the form of drops or as a thin continuous stream can be used.

The container 124 is filled with a cryogen such as Freon 122. Freon 122 has a freezing point of approximately minus 160 degrees Celsius and a boiling point of approximately minus 40 degrees Celsius. The bath 110 contains liquid nitrogen which boils at approximately minus 196 degrees Celsius.

In use of the apparatus of FIGS. 4 and 5 the material to be treated, which can be a ceramic consisting of at least two components dispersed in a liquid carrier, is fed along the pipe 142, mixed by the stirrer 140 and then fed through the nozzle 138 as a series of drops. The drops fall through the opening 122 and onto the surface of the smoothly flowing liquid cryogen in the container 124. The impeller 128 circulates the cryogen around the canal which lies vertically and encircles the spacer 126. Experimental work has shown that the drops freeze into the form of flakes on the surface of the cryogen at the location at which they enter the canal. Freezing is extremely rapid due to the fact that there is direct heat conduction from the drops to the cryogen without the formation of an insulating layer of evaporated cryogen. The ice crystals that form are thus small. Ice crystal growth does not, as a consequence, displace the particles of the ceramic mixture to a significant extent and result in a non-homogeneous mix.

The screw 130.1 lifts the frozen flakes and deposits them into the vessel 134. Because the screw is a loose fit in the casing 132, the cryogen readily flows back to the bath.

Gaseous nitrogen fills the entire bath 110 above the level of the cryogen in the container and above the level of the boiling liquid nitrogen in the bath. It flows over the edge 118 into the subsidiary compartment 114. Thus the vessel 134 is held at a low temperature. The means provided for replacing liquid nitrogen that has boiled away is not shown. Because the cryogen is maintain at a temperature which is close to its freezing point, little cryogen is lost during treatment of the material as the material does not raise the temperature of the cryogen to its boiling point. This has the further effect that no bubble layer is formed which can insulate the drop from the liquid cryogen.

To facilitate collection of the flakes by the screw 130.1, the entire apparatus is preferably elongate but narrow as best seen in FIG. 5.

Should the material being treated be heavy enough to sink in the cryogen, then means are required to collect the frozen material from the bottom of the bath. For example, the bath can be shaped so as to form a sump and a screw can be provided for lifting the flakes to the surface.

Movement of the cryogen assists in that it carries away flakes from the point at which the material encounters the cryogen. Furthermore, such movement ensures that cold cryogen is always being supplied to the point at which material enters.

Figure 6:
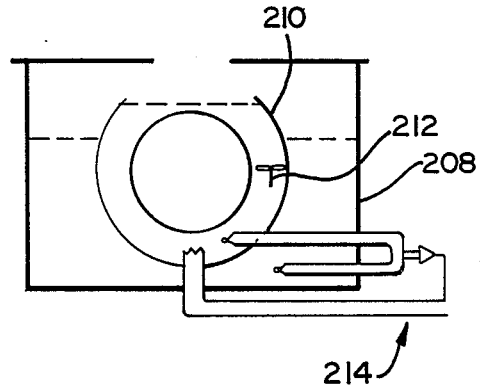
FIGS. 6 and 7 are diagrammatic side elevations of two further forms of apparatus for treating a ceramic material.

Turning now to FIG. 6, reference numeral 208 indicates a bath which contains boiling liquid nitrogen. A ring 210, arranged with its axis horizontal, has its lower portion immersed in liquid nitrogen in the bath 208 and its upper portion above the liquid nitrogen. The ring 210 forms an endless canal around which cryogen is circulated by means of an impeller 212. The ring 210 is open at its upper end so that the cryogen has an exposed upper surface. In the region of the impeller flow is turbulent so that the cryogen is mixed. This enhances the creation of a uniform temperature throughout the cryogen. Reference numeral 214 designates temperature sensing means and a heater of the same type as are shown at 136 and 137 in FIG. 4. The nozzle which feeds the ceramic into the canal at the entry location so that it falls onto the exposed surface of the cryogen has not been shown nor has the means, which can be a screw such as shown at 130 in FIG. 4, for removing cryogen flakes from the surface of the flowing cryogen.

Heat transfer from the cryogen to the liquid nitrogen in the bath 208 can be through the wall of the ring 210 or a heat exchanger can be incorporated.

Figure 7:
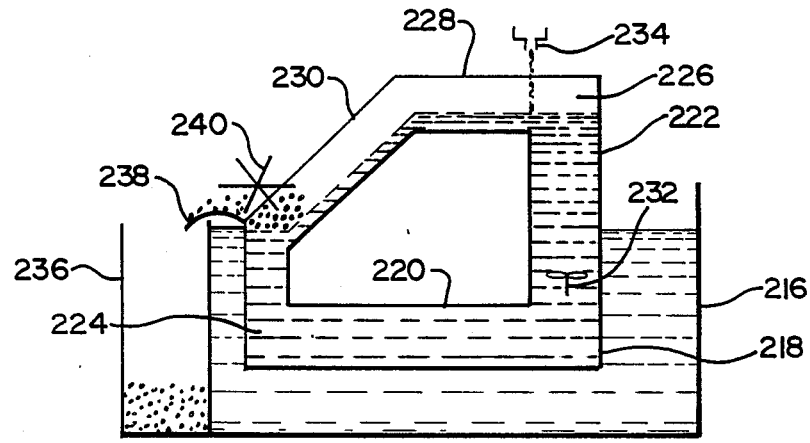

Turning now to FIG. 7, the apparatus illustrated in this Figure comprises a bath 216 which contains liquid nitrogen. Within the bath 216 there is a container 218, there being a spacer 220 within the container 218. The end wall 222 of the container 218 is of greater height than its end wall 224 and the two side walls 226 are each bounded by a horizontal upper edge 228 and a sloping upper edge 230. The shape of the spacer 220, when this is viewed in elevation, is similar to the shape of the side walls 226. An impeller 232 feeds cryogen around the endless canal provided therefor. More specifically the cryogen is fed upwardly adjacent the tall end wall 222 so that it flows onto the horizontal top surface of the spacer 220, then down the sloping surface of the spacer, between the spacer and the end wall 224 and then beneath the spacer. A nozzle for feeding onto the cryogen the material to be frozen is located at 234 and a receptacle for collecting the frozen flakes is shown at 236. A chute is shown at 238.

In use, the cryogen circulates in the canal defined by the container 218 and the spacer 220. Frozen flakes which float on the cryogen flow down the sloping face of the spacer and pile up against the top edge of the end wall 224 and on the chute 238. Once the flakes have piled up sufficiently they slide down the chute 238 into the receptacle 236. If desired a screw such as is shown at 130 in FIG. 4 can be used to assist in removing the frozen flakes. Alternately, as shown in FIG. 7, a rotatable paddle wheel 240 can be provided which pushes the piled-up flakes over the top edge of the wall 224 and into the evacuatable receptacle 236.

An advantage of the form of apparatus shown in FIG. 7 is that the cryogen has an opportunity of running off the flakes and back into the container 218 before the flakes are removed. The result of this is that cryogen loss is minimised. Temperature sensing and heating means (not shown) are also provided.

Figure 8:
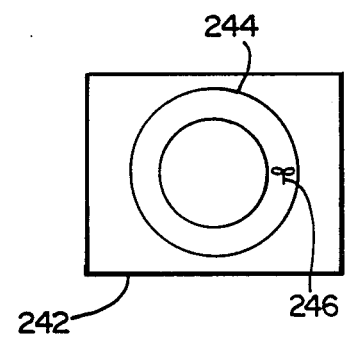
FIG. 8 is a top plan view of another form of apparatus.

Turning finally to FIG. 8, the apparatus illustrated here comprises a bath designated 242 and a container designated 244. The container is bounded by inner and outer concentric circular walls and a base wall which bound an upwardly open circular canal around which an impeller 246 circulates the cryogen. A temperature sensing and heating arrangement (not shown) of the same form as illustrated in FIG. 6 is provided. The means for dropping the material to be treated onto the surface of the cryogen and for removing the frozen flakes have not been illustrated. However, a nozzle 138 as illustrated in FIG. 4 can be used for dropping the material onto the cryogen, and a screw as shown at 130 in FIG. 4 can be used for lifting the frozen flakes from the cryogen.

If the bath of liquid nitrogen is closed and placed under a slight vacuum, violet boiling followed by freezing occurs. If this construction is used then the reference sensor of the sensing means is placed in crushed ice or in a separate container of liquid nitrogen boiling at atmospheric pressure. The cryogen in this form can itself be liquid nitrogen the temperature of which will be below its boiling point.

I claim:

1. Cryogenic apparatus comprising walling bounding an endless canal for containing liquid cryogen, means for continuously circulating liquid cryogen around said canal so that if lows past an entry location, means for introducing a substance to be frozen into the canal at said entry location so that it contacts the cryogen flowing past the entry location and is frozen by it, a bath in which said canal is located, the bath serving to hold a liquid which boils at a temperature below the freezing point of the cryogen in the canal, means for detecting the temperature of the cryogen, and heating means for maintaining the temperature of the cryogen above its freezing point but sufficiently far below its boiling point to prevent boiling occurring when the substance to be frozen is introduced.

2. Cryogenic apparatus according to claim 1, and which further comprises means above said entry location for supplying, in the form of drops or as a continuous stream, the substance to be frozen whereby the substance falls onto the surface of the flowing cryogen, and means spaced from said entry location for recovering from the cryogen the substance after it has been frozen.

3. Cryogenic apparatus according to claim 2, and further including a receptacle for receiving the recovered frozen substance, the receptacle being such that it can be evacuated to a pressure low enough to cause sublimation of any water in said recovered frozen substance.

4. Cryogenic apparatus according to claim 2, and including means for lifting floating frozen substance off the surface of said flowing cryogen.

5. Cryogenic apparatus according to claim 2, in which the means above said entry location comprises a nozzle to which said substance is supplied under pressure and stirring means upstream of the nozzle.

6. Cryogenic apparatus according to claim 2, in which said canal is bounded by inner and outer endless vertical walls the lower ends of which are joined by a bottom wall, said continuously circulating means being an impeller positioned between said inner and outer vertical walls.

7. Cryogenic apparatus, comprising walling bounding an endless canal for containing liquid cryogen, means for continuously circulating liquid cryogen around said canal so that it flows past an entry location, and means for introducing a substance to be frozen into the canal at said entry location so that it contacts the cryogen flowing past the entry location and is frozen by it, said canal being bounded by an upwardly open container for receiving liquid cryogen and by a vertical partition in said container, said means for continuously circulating liquid cryogen being arranged to displace it upwardly on one side of the partition so that it flows over the upper edge of the partition, then downwardly on the other side of the partition and thence back to said one side of the partition.

8. Cryogenic apparatus according to claim 7, in which said container is constituted by a cylinder and the partition by a tubular member inside the cylinder, there being an annular space between said cylinder and said member, and the cryogen circulating means being arranged to draw cryogen continuously from the lower end of the annular space between the cylinder and the tubular member and displace is upwardly inside the tubular member.

9. Cryogenic apparatus according to claim 7 and further comprising a bath in which said container is located, the bath serving to hold a liquid which boils at a temperature below the freezing point of the cryogen in the canal, means for detecting the temperature of the cryogen, heating means for maintaining the temperature of the cryogen above its freezing point, an outlet from the upper end of the bath, means for heating to above zero degrees centigrade cold gas which emerges from said bath through said outlet, means bounding a space above said container, and a flow path for warmed gas from the heating means to said space.

10. Cryogenic apparatus according to claim 7, and including means for holding a tissue sample and plunging it down on said one side of the partition.

11. Cryogenic apparatus comprising walling bounding an endless canal for containing liquid cryogen, means for continuously circulating liquid cryogen around said canal so that it flows past an entry location, and means for introducing a substance to be frozen into the canal at said entry location so that it contacts the cryogen flowing past the entry location and is frozen by it, said cryogenic apparatus further comprising means above said entry location for supplying, in the form of drops or as a continuous stream, the substance to be frozen whereby the substance falls onto the surface of the flowing cryogen, and means spaced from said entry location for recovering from the cryogen the substance after it has been frozen, said canal being bounded by a container having side and end walls and a bottom wall, a spacer in said container, the spacer being spaced from said end and bottom walls of the container whereby the canal passes upwardly between the spacer and an end wall, over the top of the spacer, downwardly between the spacer and the other end wall, and then between the spacer and the bottom wall.

12. Cryogenic apparatus according to claim 11, in which at least part of the upper surface of said spacer slopes whereby cryogen flows down said sloping surface, said entry location being above the spacer.

13. A method of treating a material consisting of at least two components which comprises preparing a homogeneous dispersion of the components in a liquid carrier, feeding the material onto the surface of flowing liquid cryogen at an entry location, recovering the floating frozen material from the surface of the cryogen at a location spaced from the entry location, and sublimating the frozen material.

14. A method of freezing a mechanically held tissue sample which method comprises circulating liquid cryogen upwardly on one side of a vertical partition so that it flows over the partition, down the other side of the partition and thence back to said one side of the partition, and plunging said mechanically held tissue sample downwardly into the cryogen which is flowing upwardly on said one side of the partition.

15. A method according to claim 14, in which said liquid cryogen flows upwardly inside a cylindrical member and then radially outwardly in all directions to flow over the upper edge of the cylindrical member, and said tissue sample is plunged downwardly along a line which is co-incident with the axis of said cylindrical member.

16. A method according to claim 14 and comprising the step of causing gas at above 0 degrees centigrade to flow across the surface of the cryogen thereby to sweep away evaporated cryogen and prevent build-up of a layer of gaseous cryogen above the liquid cryogen.

17. A method according to claim 16, in which said cryogen is maintained at a temperature below its boiling point by partly immersing the vessel containing the cryogen in a boiling liquid, the gases evolved from the boiling liquid being heated to above 0 degrees centigrade and caused to flow across the surface of the cryogen.

18. A method of treating a material consisting of at least two components which comprises preparing a homogenous dispersion of the components in a liquid carrier, feeding the material onto the surface of flowing liquid cryogen at an entry location, and recovering the floating frozen material from the surface of the cryogen at a location spaced from the entry location.

19. Cryogenic apparatus comprising walling bounding an endless canal for containing liquid cryogen, means for continuously circulating liquid cryogen around said canal so that it flows past an entry location, means for introducing a substance to be frozen into the canal at said entry location so that it contacts cryogen at the entry location and is frozen by it, a bath in which said canal is located, the bath serving to hold a liquid which boils at a temperature below the freezing point of the cryogen in the canal, means for detecting the temperature of the cryogen, and heating means for maintaining the temperature of the cryogen above its freezing point but sufficiently far below its boiling point to prevent boiling occurring when the substance to be frozen is introduced.

* * * * *